United States Patent
Madden et al.

(10) Patent No.: US 6,249,076 B1
(45) Date of Patent: Jun. 19, 2001

(54) CONDUCTING POLYMER ACTUATOR

(75) Inventors: John D. Madden; Tanya S. Kanigan, both of Somerville; Serge Lafontaine; Ian W. Hunter, both of Lincoln, all of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/292,041

(22) Filed: Apr. 14, 1999

Related U.S. Application Data
(60) Provisional application No. 60/081,752, filed on Apr. 14, 1998.

(51) Int. Cl.$^7$ .................................................... H01L 41/04
(52) U.S. Cl. ............................................ 310/363; 310/800
(58) Field of Search ................................... 310/363, 364, 310/365, 800

(56) References Cited

U.S. PATENT DOCUMENTS

| | | | |
|---|---|---|---|
| 5,100,933 | 3/1992 | Tanaka et al. | 523/300 |
| 5,384,029 * | 1/1995 | Campbell | 204/415 |
| 5,389,222 | 2/1995 | Shahinpoor | 204/299 |
| 5,556,700 | 9/1996 | Kaneto et al. | 428/322 |
| 5,766,013 * | 7/2000 | Vuyk | 434/114 |
| 6,084,321 * | 7/2000 | Hunter et al. | 310/20 |
| 6,109,852 | 8/2000 | Shahinpoor et al. | 414/1 |

FOREIGN PATENT DOCUMENTS

| | | | |
|---|---|---|---|
| 37 18 604 * | 7/1952 | (DE) | 310/363 |
| 762874 * | 7/1952 | (DE) | 310/363 |
| 2062930AA | 12/1994 | (ES) | H01B/1/12 |

OTHER PUBLICATIONS

Yamaura, et al., "Enhancement of Electrical Conductivity of Polypyrrole Film by Stretching: Counter Ion Effect," *Synthetic Metals*, vol. 26, pp. 209–224, Jul. 14, 1988.

Hagiwara, et al., "Enhancement of the Electrical Conductivity of Polypyrrole Film by Stretching: Influence of the Polymerization Conditions," *Synthetic Metals*, vol. 36, pp. 241–252, Dec. 1990.

Yamaura, et al., "Memory effect of electrical conductivity upon the counteranion exchange of polypyrrole films," *Synthetic Metals*, vol. 48, pp. 337–354, Dec. 1992.

Hunter, et al., "A Comparison of Muscle with Artificial Actuators," *Technical Digest of the 5$^{th}$IEEE Workshop on Sensors & Acuators*, 5, pp. 178–185, Dec. 1992.

Sailor, et al., "Conducting Polymer Connections for Molecular Devices," *Advanced Materials*, 6, No. 9, Dec. 1994.

Baughman, "Conducting polymer artificial muscles," *Synthetic Metals*, 78, pp. 339–353, Dec. 1996.

Sapp, et al., "Rapid Switching Solid State Electrochromic Devices Based on Complementary Conducting Polymer Films," *Advanced Materials*, 8, No. 10, pp. 808–811, Dec. 1996.

Santa, et al., "Characterization and modelling of a conducting polymer muscle–like linear actuator," *Smart. Mater. Struct.*, 6, pp. 23–34, Dec. 1997.

Mazzoldi, et al., "Actuative properties of polyaniline fibers under electrochemical stimulation," *Materials Science and Engineering*, C6, pp. 65–72, Dec. 1998.

\* cited by examiner

*Primary Examiner*—Thomas M. Dougherty
(74) *Attorney, Agent, or Firm*—Bromberg & Sunstein LLP

(57) ABSTRACT

Embodiments of actuators having an active member including a polymer having a surface, an electrolyte coupled to the surface, and an electrolyte are provided. Actuators which, when an electrical potential is applied across the electrolyte between the active member and the counter electrode, exert force per unit area of at least 10 MPa are described. Particular designs utilizing stretch aligned conducting polymers as active members are discussed.

43 Claims, 5 Drawing Sheets

CONDUCTING POLYMER ACTUATOR

RELATED U.S. APPLICATION(S)

The present application claims priority from Provisional Application Ser. No. 60/081,752, filed Apr. 14, 1998 which is hereby incorporated herein by reference.

FIELD OF THE INVENTION

This invention relates to an actuator which has a conducting polymer as its active component and is capable of operation outside of a bulk liquid environment.

BACKGROUND ART

Conducting polymers are a class of polymers which structurally feature a conjugated backbone and are electronically conductive. Some common conducting polymers are polyaniline, polypyrrole and polyacetylene. These materials are semi-conductors in their pure form. However, upon oxidation or reduction of the polymer, conductivity is increased. The oxidation or reduction leads to a charge imbalance which, in turn, results in a flow of ions into the material in order to balance charge. These ions or dopants enter the polymer from a surrounding, ionically conductive electrolyte medium. The electrolyte may be a gel, a solid, or a liquid. If ions are already present in the polymer when it is oxidized or reduced, they may exit the polymer.

In addition, it is well known that dimensional changes may be effectuated in certain conducting polymers by the mass transfer of ions into or out of the polymer. In some conducting polymers, the expansion is due to ion insertion between chains, whereas in others interchain repulsion is the dominant effect. Thus, the mass transfer of ions both into and out of the material leads to a contraction or expansion of the polymer. Typical volume changes are on the order of 10%, and linear dimensional changes are hence on the order of 3%. Stresses observed in current conducting polymer materials are on the order of 3 MPa.

Conducting polymer actuators are typically configured by immersion of the polymer in an environment of a bulk liquid electrolyte. Encapsulated conducting polymer actuators known in the art are limited to bilayers comprising multiple conducting polymer films in which a differential contraction and bending is induced.

Copending U.S. patent applications Ser. Nos. 09/130,500, filed Aug. 7, 1998, entitled "Conducting Polymer Driven Rotary Motor," 09/204,929, filed Dec. 3, 1998, entitled "Method of Manufacture of Polymer Transistors with Controllable Gap," and 09/263,980, filed Mar. 5, 1999, entitled "Conducting Polymer Generator-Actuator with Energy Storage/Recovery," disclose other applications for conducting polymers and are hereby incorporated herein by reference.

SUMMARY OF THE INVENTION

In accordance with an embodiment of the present invention, an actuator has an active member, an electrolyte coupled to the surface, and a counter electrode coupled to the electrolyte. The active member has a surface, a member volume, a length, and an axis. The active member includes a polymer. The application of an electrical potential across the electrolyte between the active member and the counter electrode causes the member to exert, essentially along the axis, a force per unit area of at least 10 MPa. Additionally, the actuator may have a flexible skin for separating the electrolyte from an ambient environment.

In accordance with alternate embodiments of the invention, the active member may be a film, a fiber, or a set of substantially parallel fibers. The conducting polymer may, preferredly, be polypyrrole. The electrolyte may be a gel which preferredly includes agar. In another embodiment, the volume of electrolyte is at least five times the member volume. The counter electrode may be a coiled metal wire, a metallic thin film, or a conducting polymer and distributed substantially over the length of the active member. Application of the electrical potential may selectively activate only some of a set of substantially parallel fibers.

In yet another embodiment, the counter electrode may be a second active member. Such an actuator may further be configured so that stresses may be generated by each member in opposite directions along the axis. The members may cause a torque to be applied to a drive arrangement included as part of the actuator embodiment.

In a further embodiment, an actuator has an electrically deformable conducting polymer active member having a surface and an axis, an electrolyte coupled to the surface, a counter electrode coupled to the electrolyte, and a housing. The member, the electrolyte and the counter electrode are located substantially within the housing. The application of an electrical potential across the electrolyte between the member and the counter electrode causes the member to deformessentially along the axis. The housing may be made of polypropylene. The housing may have a wall thickness which is no more than 20% of an actuator dimension measured along a common axis to the thickness measurement normal to the axis.

In a further embodiment, an actuator has an active member which includes a polymer and a plurality of electrically conductive attachment areas spaced at locations along its length, an electrolyte and a counter electrode. The application of an electrical potential across the electrolyte and an area causes the member to deform.

BRIEF DESCRIPTION OF THE DRAWINGS

The invention will more readily be understood by reference to the following description taken with the accompanying drawings.

The drawings are intended to provide a better understanding of the present invention, but are in no way intended to limit its scope.

DETAILED DESCRIPTION OF SPECIFIC EMBODIMENTS

Figure 1:
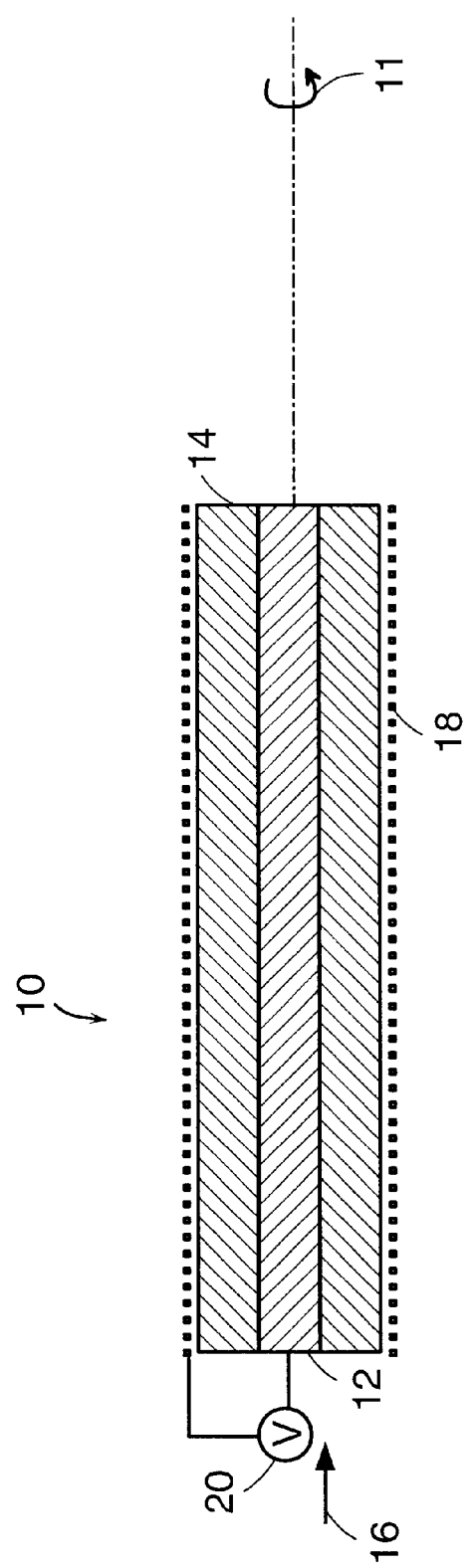
FIG. 1 depicts a schematic cross-sectional view of a polymer actuator in accordance with an embodiment of the invention.

Referring to FIG. 1, an actuator 10 is shown schematically in cross-section, in accordance with an embodiment of the invention. Active member 12 of actuator 10 has a surface coupled with electrolyte 14 and has an axis 11. Active member 12 preferably includes a conducting polymer contracting or expanding in response to the flow of ions out of, or into, the member. Ions are provided by electrolyte 14 which adjoins member 12 over at least a portion, up to the entirety, of the surface of member 12 in order to allow for the flow of ions between the two media. Many geometries are available for the relative disposition of member 12 and electrolyte 14. In accordance with preferred embodiments of the invention, member 12 may be a film, a fiber or a group of fibers, or a combination of multiple films and fibers disposed so as to act in concert for applying a tensile force in a longitudinal direction substantially along axis 11. The fibers may be bundled or distributed within the electrolyte 14.

Note that conducting polymers are different from other electro-responsive polymers described in the literature. Polymers described, for example, in U.S. Pat. No. 5,389,222, entitled "Spring-Loaded Polymeric Gel Activators" to Shahinpoor, and in U.S. Pat. No. 5,100,933, entitled "Collapsible Gel Compositions" to Tanaka, are gels and are not electronically conductive. Any conduction exhibited by these gels occurs strictly by the transfer of ions. In contrast, in conducting polymers, charge is transported along the polymer backbone and between chains. Two important distinctions result. First, the electronic conductivity of conducting polymers means that there is less need to rely on interpenetrating electrodes for electrical charge transport. Shahinpoor, for example, employs platinum dendrite electrodes to make electrical contact within gel films. Second, the electroactive polymers are gels which have large solvent contents. As a result, they are not as mechanically stiff as the conducting polymer films or fibers and cannot generate forces per unit area as high as those achievable in conducting polymer actuators.

In accordance with an embodiment of the invention, active member 12 includes a conductive polymer. Many conductive polymers having desirable tensile properties are known to persons skilled in the art. In accordance with a preferred embodiment of the invention, active member 12 is a polypyrrole film. Such a polypyrrole film may be synthesized by electrodeposition according to the method described by M. Yamaura et al., "Enhancement of Electrical Conductivity of Polypyrrole Film by Stretching: Counter-ion Effect," *Synthetic Metals*, vol. 36, pp.209–224 (1988), which is incorporated herein by reference. By employing the procedure described by Yamaura et al., film dimensions range typically from between 20–40 microns thick and 10 mm wide by 30 mm long. Tensile strengths in excess of 25 Mpa are routinely achieved. In addition to polypyrrole, any conducting polymer that exhibits contractile properties may be used within the scope of the invention. Polyaniline is an example of such a usable conducting polymer. Additionally, non-conducting polymers may be used in embodiments of the actuators described below when they are electrochemically activated by means of interpenetrating conducting networks. The formation of the member 12 in the actuator embodiments into a film or fiber form may be by electrochemical means, as described, for example, by Yamaura et al., by chemical or by any other means known in the art of materials processing.

In accordance with an embodiment of the invention, the polymer films are stretch aligned along a long axis (later denoted as the axis 11). This is done by immersing the polymer in propylene carbonate at between 40° C. and 50° C. The polymer is clamped at either end and stretched to between 0.6 and 1.2 times its original length. This processing has the effect of aligning the molecules within the polymer along the stretching direction, thereby increasing conductivity (to 40,000 S/m or greater),increasing creep resistance, and increasing tensile strength to values greater than 60 Mpa. Tensile strength can be further increased by employing fine fibers, as known in the art of materials processing, to achieve tensile strengths in excess of 100 Mpa. We have discovered that stretch aligned polypyrrole films produce current-induced strains at tensile force levels of 35 MPa. Further, we found that stretch alignment does not reduce the strain produced with a given applied charge. The ratio of strain produced to applied charge remains fairly constant and is essentially independent of the level of applied stress.

Electrolyte 14 may be a liquid (which may require actuator encapsulation), a gel, or a solid, within the scope of the invention and of the appended claims. In accordance with an embodiment of the invention, electrolyte 14 may be a gel. Citing specific examples without limitation, an agar or polymethylmethacrylate (PMMA) gel containing a salt dopant are superior candidates. In the case of agar, aqueous 1 M tetraethyl ammonium hexafluorophosphate with 1 g of agar are added per 150 ml of water. Additionally, other ions may be employed as known in the art. The mixture is heated to thicken according to procedures known in the art. As an alternative example of an electrolyte 14 gel that may be employed, PMMA gel may be synthesized following the procedure given by S. A. Sapp, G. A. Sotzing, J. L. Reddinger, J. R. Reynolds, p. 808 (1996), which volume is herein incorporated by reference. The requisite volume of electrolyte 14 is determined by the ionic concentration of the electrolyte (e.g. by the salt concentration in the gel). In a preferred embodiment, a conducting polymer active member 12 will transfer up to a maximum of one ion for every three monomers. Given the typical dimensions of a polypyrrole member, a gel layer having a thickness between 100 microns and 1 mm is preferred. Higher salt concentrations in the gel would, however, permit reduced thicknesses of gel. It may even be possible to have an electrolyte 14 thickness which is smaller than that of member 12. It is, furthermore, desirable that electrolyte 14 be substantially compliant so as to reduce mechanical constraints upon the deformation of active member 12. By employing another conducting polymer to serve as the counter electrode 18, the electrolyte layer 14 can be made equal or smaller in volume to active member 12. This is because the counter electrode 18 will tend to absorb any ions that flow out of the member 12. Typically, each polymer (member 12 and counter electrode 18) will experience a strain that is opposite in sign to the strain in the other. This effect is taken advantage of to produce an embodiment of a rotational actuator, as described below in FIG. 5.

Counter electrode 18 is in electrical contact with electrolyte 14 in order to provide a return path for charge to source 20 of potential difference between member 12 and electrolyte 14. In an embodiment of the invention, counter electrode 18 is 25 micron diameter gold wire, wound around the outside of electrolyte 14. Counter electrode 18 may be any electrical conductor, and, in accordance with alternate embodiments of the invention, counter electrode 18 may be another conducting polymer, a conducting polymer gel, a metal, or in general an electronically conductive material. It is desirable to reduce the mechanical impedance to deformation of the active member 12, and thus counter electrode 18 may itself be a conducting polymer actuator contracting in the same sense as member 12. Conversely, counter electrode 18 may expand as member 12 contracts, and counter electrode 18 and member 12 may be mechanically decoupled as is the case in contralateral muscle.

In order to activate actuator 10, a current is passed between active member 12 and counter electrode 18, inducing contraction or expansion of member 12. Referring now to Example 1, the strain (under isotonic conditions) and the stress (under isometric conditions) are substantially proportional (over a limited linear range) to the charge transferred into or out of active member 12. Typical currents, in accordance with a preferred embodiment of the invention, are on the order of 10 mA, while typical voltages applied by source 20 (which may be any source of electrical potential known in the art) are on the order of ±(0.1–10) V. The range of linear response to charge is limited, with typical strains being approximately 2 to 5%. The relationship between stress σ, strain ε, charge flow density per unit polymer volume per unit time, and time t, can be approximated by:

$$\sigma = E\epsilon - E\alpha \int 92 dt,$$

where E is the modulus of elasticity of the actuator and α is the strain/charge density ratio. The strain-to-charge density ratio depends on the material, the ion and the solvent, but is typically in the range of $10^{-11}$ to $10^{-10}$ $C^-m^3$ for polypyrrole and polyaniline in aqueous propylene carbonate and gel electrolyte solutions.

An important distinction between the present invention and prior art is that the actuator embodiments disclosed herein act in a linear fashion to generate force, torque and displacement. Prior art involves bilayer actuators in which two or more materials, including at least one actively deforming material, form a laminate structure. The deformation of the active material results in a bending of the structure. As is known in the art of mechanics of materials, such laminate structures produce large displacements but small forces as compared to linear actuators. In applications such as protheses, large forces are required, making bilayer actuators impractical. The obstacle to date in making effective linear actuators has been the lack of appropriate

EXAMPLE 1

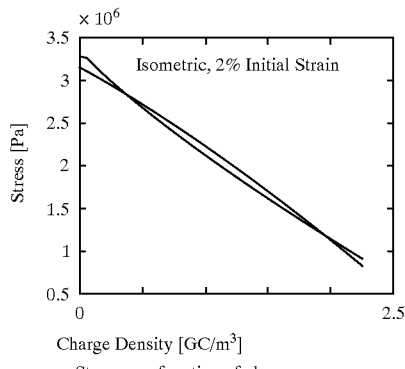

Stress as a function of charge.

EXAMPLE 1-continued

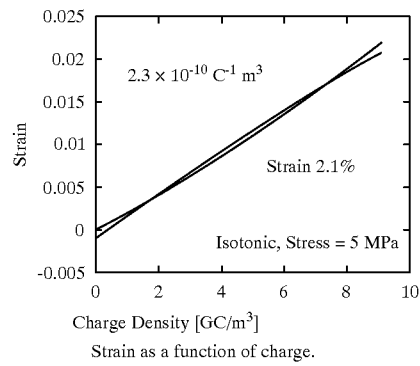

Strain as a function of charge.

methods of encapsulation, which enable ready and virtually unimpeded linear displacement of the actuator.

Figure 2:
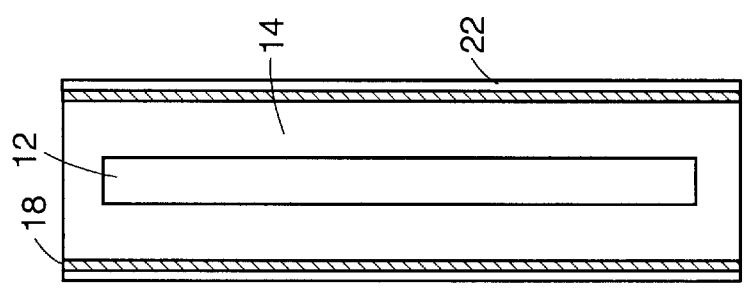
FIG. 2 is a cross-sectional view of an encapsulated polymer actuator in accordance with another embodiment.

FIG. 2 illustrates a cross-sectional view (with axis 11 into the plane of the view) of an encapsulated actuator embodiment. To clarify the relative dimensions of the actuator elements, active element 12 may be a 40 micron thick sheet of polypyrrole, while the electrolyte 14, which may preferably be an agar gel, may be on the order of 100 microns thick. Counter electrode 18 is less than 100 nanometers, while housing 22 may be on the order of a few microns. In this embodiment, the counter electrode 18 may be a metallic thin film of gold, palladium, platinum, or other alloy. Counter electrode 18 may be deposited onto housing 22. For example, polyethylene or other suitable material for housing 22 may be sputter coated with a gold-palladium alloy which would serve as counter electrode 18.

Figure 3:
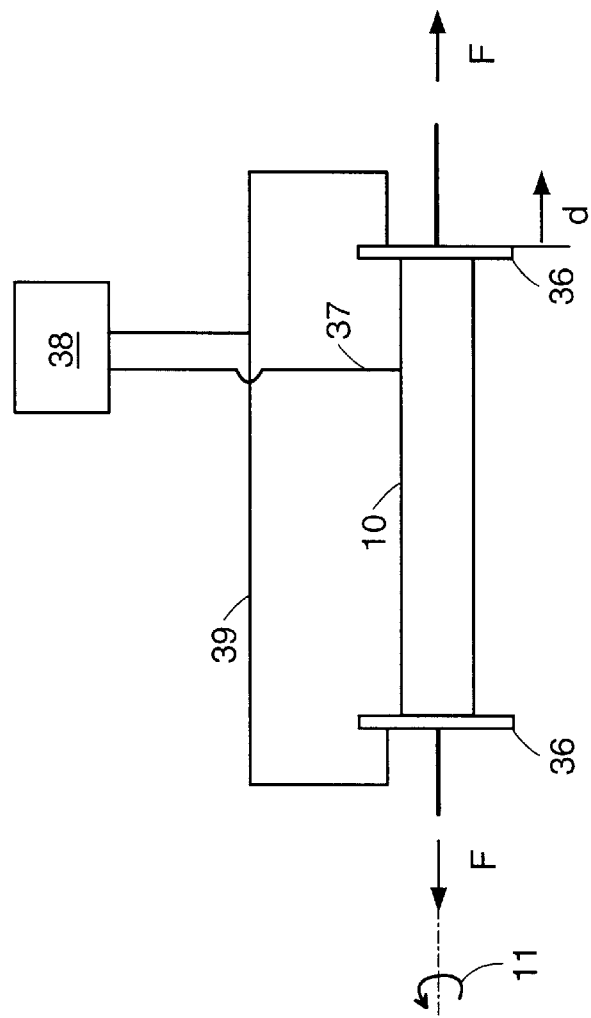
FIG. 3 is a schematic longitudinal view of a polymer actuator and associated electrical and mechanical couplings in accordance with an embodiment.
Figure 4:
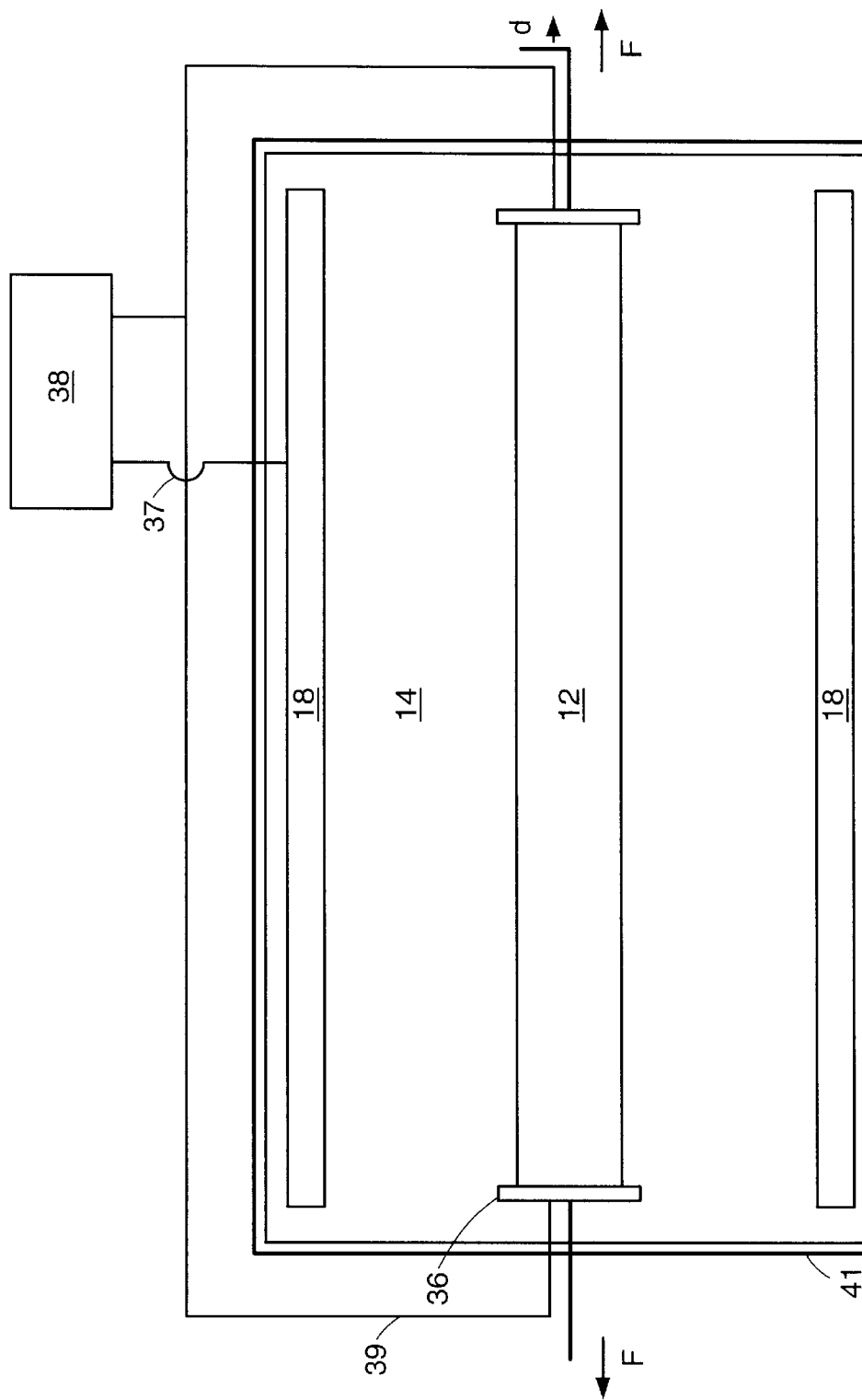
FIG. 4 shows another embodiment of an encapsulated actuator depicted in a schematic cross-sectional view.

Referring to FIG. 3, conducting clamps 36 are attached to both ends of actuator 10. Clamps 36 provide both electrical and mechanical couplings to the actuator 10. Actuator performance may be tested by applying force F along axis 11. Displacement d may be measured with applied force F combined with expansion or contraction of the actuator 10 caused by the mass transfer of ions into or out of the conducting polymer member when an electrical potential is applied. The voltage source is provided by electrical pathways 37, to the counter electrode, and 39, to the member through clamps 36, from the power supply 38. Example 2 shows the strain induced in an actuator of the embodiment depicted in FIG. 3. A +20 ma current is applied for eighty seconds, followed by a current of −80 ma for 80 seconds. A 2% strain is induced with the actuator 10 experiencing a constant stress of 2 MPa along the axis 11. FIG. 4 illustrates a similar embodiment depicting an encapsulated actuator. In this embodiment, liquid electrolyte 14 might effectively replace the gel described above. Housing 41 shields the electrolyte 14 from the ambient environment. Alternatively, gel may be used in such an encapsulated actuator 10. Drying of gel electrolyte, particularly near the clamps 36 might be minimized by this design. Such drying tends to constrain movement of active member 12 and is detrimental when attempting to maximize the force and displacement capabilities of actuator 10 as described above. When PMMA gel is employed, the ends need not be sealed as the drying of the exposed gel protects the gel inside from desiccation.

EXAMPLE 2

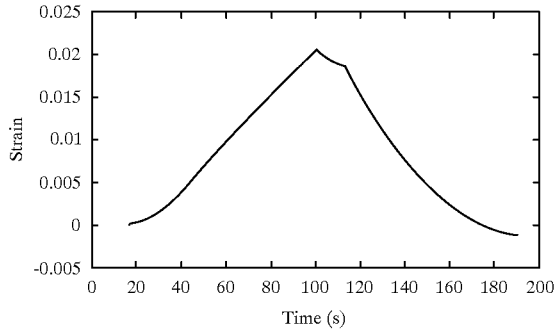

Strain in an encapsulated linear actuator with 2 MPa applied stress, in response to a ±20 mA current.

Figure 5:
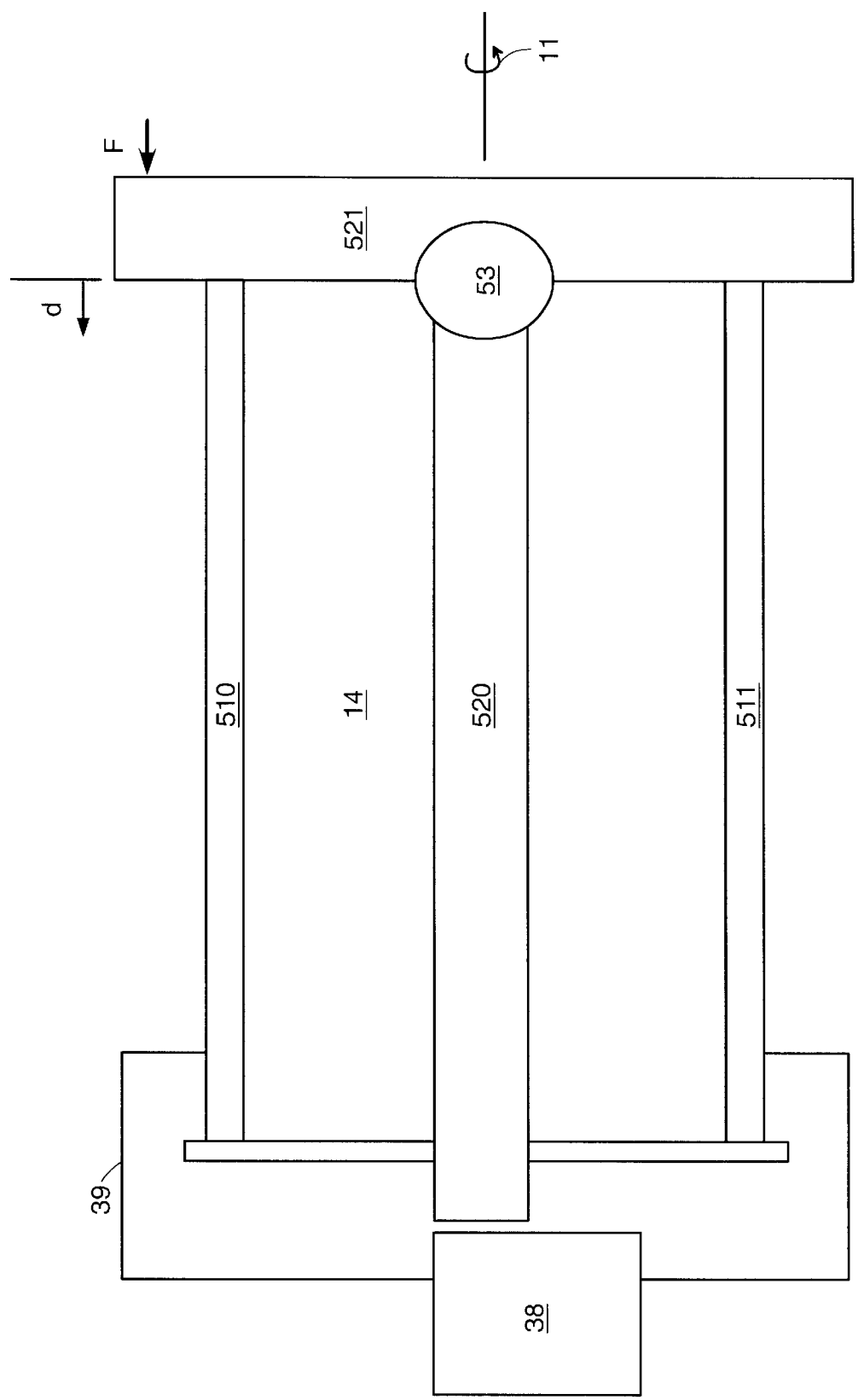
FIG. 5 is a schematic cross-sectional view of an actuator featuring two active members.

FIG. 5 is a schematic cross-sectional view of an actuator featuring two active members. Active members 510 and 511 act as counter electrodes for each other. Electrical coupling is achieved as shown by pathway 39 from power supply 38. With the application of electrical potential between members 510 and 511, first member 510 may contract while second member 511 may expand as ions flow into and out of the members and electrolyte 14. Because active members 510 and 511 act in opposite fashion (one expands, the other contracts) along axis 11, the result is a rotation of passive member 521 relative to second passive member 520 about bearing 53. Activation of the embodiment of FIG. 5 also results in a torque being developed about bearing 53. Bearing 53 may be a flexural element or other rotary bearing known in the art. The extent of angular rotation of passive member 521 is a function of the relative placement of active members 510 and 511, their lengths, and the strain induced in them. Unlike other embodiments in which the electrolyte 14 serves to store, as well as, transfer charge, only charge transfer is required here. This is because the active members 510 and 511 will store charge. Consequently, the volume of electrolyte 14 may be small relative to the volume of the members 510 and 511.

Figure 6:
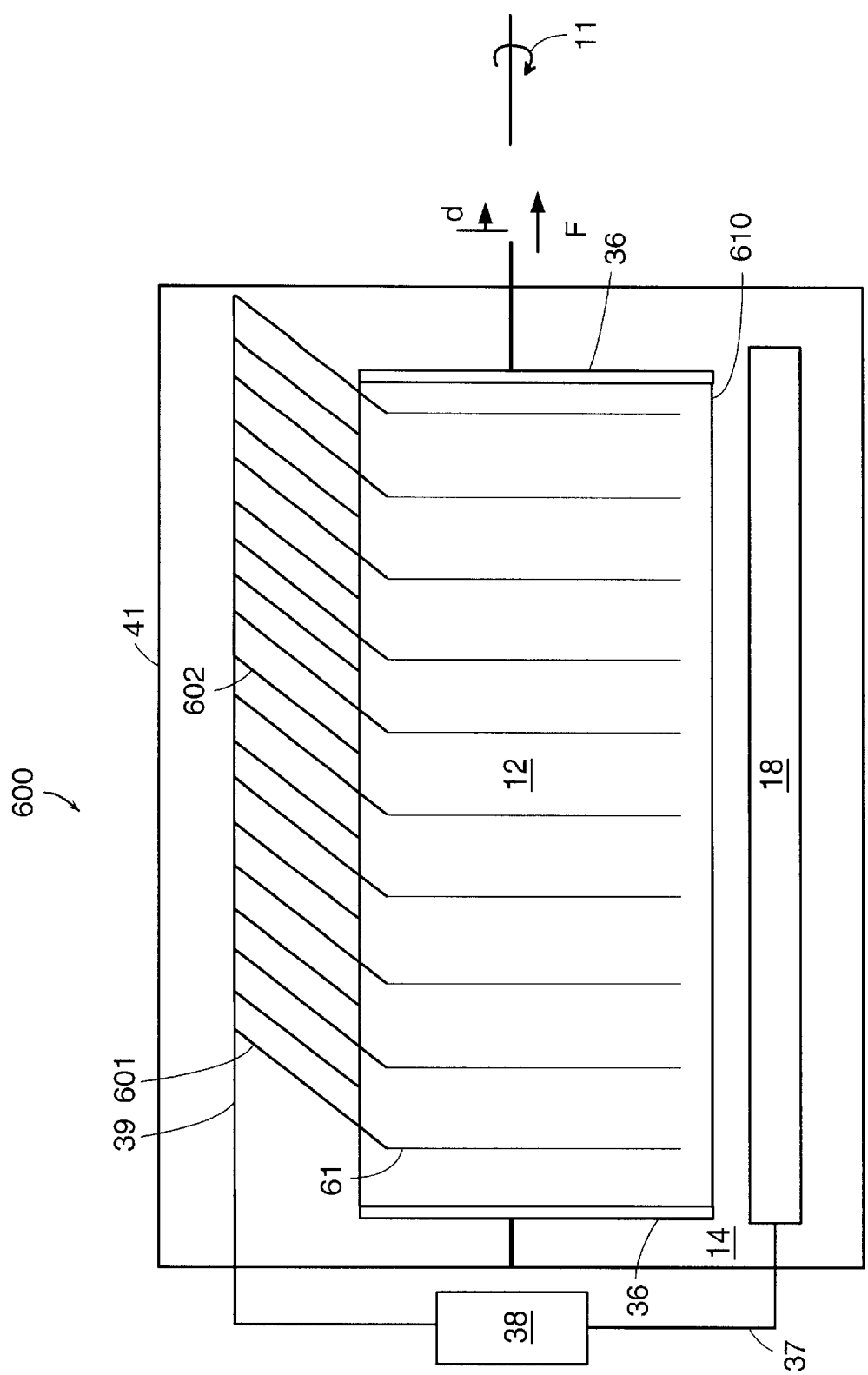
FIG. 6 is a schematic cross-sectional view of a distributed actuator in accordance with an embodiment of the invention.

Referring to FIG. 6, a distributed actuator 600 is shown schematically in cross-section, in accordance with an embodiment of the invention. The term "distributed actuator" 600 refers to the distribution of electrical current passed into active member 12 at a plurality of locations rather than only proximal to ends 610 of member 12. Charge is injected into the active member 12 via charge path 39. The current flowing through path 39 is divided between a plurality of charge paths 601 and 602 which electrically couple to active member 12 through conductive areas 61. Thus, a pathway from the power supply 38 to the active member 12 is completed. The areas 61 are shown spaced along the length of (axis 11) active member 12. Many geometries are available for the relative disposition of member 12 and contact areas 61. These areas 61 may be located on the surface or within the active member 12, and spaced within any member 12 dimension. Charge paths 602, as illustrated in FIG. 6, are coupled to areas 61 not visible in FIG. 6. In accordance with another embodiment of the invention, contact areas 61 may be equally spaced along the length of active member 12. In an embodiment, contact areas 61 consist of approximately 25 micron diameter gold wires embedded within active member 12. The embedding of the gold wires 61 is achieved via electrochemical fusion, wherein the gold wires 61 are placed next to the active member in an electrode position cell. Electrode position proceeds, as is described above for polypyrrole member 12, except that the wires 61 are held at the same electrical potential as the polypyrrole film, leading to a further deposition of polypyrrole both on the growing polypyrrole film and the gold wires 61. Wires 61 are joined to the film through the newly grown material. Charge paths 601 and 602 are continuations of the 25 micron gold wires 61 embedded within the active member 12. Further, these wires 601 and 602 may be electrically insulated to reduce undesirable interaction with the electrolyte 14. Unlike the embodiments previously described, current is applied in a distributed manner via contact areas 61. The advantage of employing the electrode geometry shown in FIG. 6 is related to the speed and efficiency of actuator 600 operation. The higher the current transferred, the faster the response of actuator 600, since the generation of force and displacement are proportional to charge transferred. However, active member 12 has a finite resistance. For example, in the case that the member 12 is a polypyrrole film 40 mm long by 10 mm wide by 30 microns thick, the resistance along the axis 11 is roughly 5 ohms. When current is passed only through the ends 610, a potential difference develops between the middle of the member 12 and the ends 610. This drop is particularly significant at high currents and results in a lowering of actuator 600 efficiency. By making a plurality of electrical contact areas 61 to the active member 12, the potential drop is substantially reduced and efficiency is maintained even at higher currents. Further, the active member 12 has an associated capacitance per unit volume. 50 mg of polypyrrole may have a capacitance on the order of 1 Farad. The speed at which charging can occur is thus limited by an RC (resistor-capacitor) charging time, as is know in the electronics art. The effect of multiple contacts 61 is to reduce the RC charging time by dividing the active member resistance and capacitance in parallel. The RC charging time due to the active member impedance is thus reduced roughly in proportion to the number of contact areas 61. The parallel contacts allow an increase in the strain rate from 0.01%/s typical of linear actuators to greater than 0.5%/s. Further increases in performance can be obtained by reducing the member thickness, thereby allowing more rapid transit of ions in and out of the material, and by reducing electrolyte impedance.

Although the invention has been described with reference to several preferred embodiments, it will be understood by one of ordinary skill in the art that various modifications can be made without departing from the spirit and the scope of the invention, as set forth in the claims hereinbelow.

We claim:
1. An actuator comprising:
   an electrolyte;
   a counter electrode coupled to the electrolyte; and
   an active member comprising a polymer, the active member having an axis, a length defined along the axis, and having a surface coupled to the electrolyte, the active member capable of exerting, essentially along the axis, a force per unit area of at least 10 MPa concurrent with application of an electrical potential between the active member and the counter electrode.
2. An actuator according to claim 1, further comprising:
   a flexible skin for separating the electrolyte from an ambient environment.
3. An actuator according to claim 1, wherein the polymer is selected from conducting polymers and non-conducting polymers, the non-conducting polymers having associated interpenetrating conducting networks.
4. An actuator according to claim 1, wherein the electrolyte is a liquid.

5. An actuator according to claim 4, wherein the liquid is propylene carbonate.

6. An actuator according to claim 5, wherein a salt is added to the propylene carbonate, the salt being tetraethylammonium hexafluorophosphate.

7. An actuator according to claim 3, wherein the polymer is a conducting polymer.

8. An actuator according to claim 7, wherein the active member is a film.

9. An actuator according to claim 7, wherein the active member is a fiber.

10. An actuator according to claim 7, wherein the active member is a set of substantially parallel fibers.

11. An actuator according to claim 10, wherein the application of the electrical potential activates at least one of the set of fibers.

12. An actuator according to claim 7, wherein the conducting polymer is polypyrrole.

13. An actuator according to claim 12, wherein the electrolyte is a gel.

14. An actuator according to claim 13, wherein the gel includes agar.

15. An actuator according to claim 14, the electrolyte having an electrolyte volume and the active member having a member volume, wherein the electrolyte volume is equal to at least five times the member volume.

16. An actuator according to claim 15, wherein the counter electrode is distributed substantially over the length of the active member and comprises a coiled metal wire.

17. An actuator according to claim 7, wherein the counter electrode is distributed substantially over the length of the active member and comprises a conducting polymer.

18. An actuator according to claim 17, wherein the counter electrode is a second active member, the electrical potential applied between the active members across the electrolyte.

19. An actuator according to claim 18, further comprising:
    a drive arrangement;
so that the application of the electrical potential causes the active member and the second active member to exert forces in opposite directions essentially along the axis, resulting in torque being applied to the drive arrangement.

20. An actuator according to claim 1, wherein the electrolyte is a gel.

21. An actuator according to claim 1, wherein the counter electrode is distributed substantially over the length of the active member and comprises a coiled metal wire.

22. An actuator according to claim 1, wherein the counter electrode is distributed substantially over the length of the active member and comprises a metallic thin film.

23. An actuator according to claim 22, wherein the metallic thin film contains a metal selected from gold, palladium, platinum and combinations thereof.

24. An actuator comprising:
    an electrically deformable, conducting polymer active member having a surface, a member volume, a length and an axis;
    an electrolyte, having an electrolyte volume, coupled to the surface of the active member;
    a counter electrode coupled to the electrolyte; and
    a housing, including side walls, having an interior surface;
so that the active member, the electrolyte and the counter electrode are located substantially within the housing, the active member spatially displaced from the interior surface, and so that application of an electrical potential between the active member and the counter electrode causes the active member to deform essentially along the axis without exerting force on the walls.

25. An actuator according to claim 24, wherein the active member is a film.

26. An actuator according to claim 24, wherein the active member is a fiber.

27. An actuator according to claim 24, wherein the active member is a set of substantially parallel fibers.

28. An actuator according to claim 27, wherein the application of the electrical potential causes at least one of the set of fibers to deform.

29. An actuator according to claim 24, wherein the conducting polymer is polypyrrole.

30. An actuator according to claim 29, wherein the electrolyte is a gel.

31. An actuator according to claim 30, wherein the gel includes agar.

32. An actuator according to claim 31, wherein the electrolyte volume is equal to at least five times the member volume.

33. An actuator according to claim 32, wherein the counter electrode is distributed substantially over the length of the active member and is a coiled metal wire.

34. An actuator according to claim 24, wherein the electrolyte is a gel.

35. An actuator according to claim 24, wherein the counter electrode is distributed substantially over the length of the active member and is a coiled metal wire.

36. An actuator according to claim 24, wherein the counter electrode is distributed substantially over the length of the active member and is a conducting polymer.

37. An actuator according to claim 36, wherein the counter electrode is a second active member, the electrical potential applied between the active members across the electrolyte.

38. An actuator according to claim 37, further comprising:
    a drive arrangement;
so that the application of the electrical potential causes the active member and the second active member to exert forces in opposite directions essentially along the axis, resulting in torque being applied to the drive arrangement.

39. An actuator according to claim 24, wherein the counter electrode is distributed substantially over the length of the active member and is a metallic thin film.

40. An actuator according to claim 39, wherein the metallic thin film contains a metal selected from gold, palladium, platinum and combinations thereof.

41. An actuator according to claim 24, wherein the housing is made from polyethylene.

42. An actuator according to claim 41, the housing having a wall thickness, wherein the thickness is no more than 20% of an actuator dimension, the actuator dimension and the wall thickness measured along a common axis normal to the axis of the active member.

43. An actuator comprising:
    an active member having a surface, a member volume, a length, and an axis, the active member including a polymer and including a plurality of electrically conductive attachment areas, the areas spaced at locations along the length;
    an electrolyte, having an electrolyte volume, coupled to the surface of the active member;
    and a counter electrode coupled to the electrolyte;
so that application of an electrical potential between the counter electrode and an area causes the active member to deform essentially along the axis.

* * * * *

UNITED STATES PATENT AND TRADEMARK OFFICE
CERTIFICATE OF CORRECTION

| | |
|---|---|
| PATENT NO. | : 6,249,076 B1 |
| DATED | : June 19, 2001 |
| INVENTOR(S) | : John D. Madden et al. |

It is certified that error appears in the above-identified patent and that said Letters Patent is hereby corrected as shown below:

<u>Column 1,</u>
Line 2, please insert the following aknowledgement as the first paragraph of the text of the patent as requested by the U.S. Government.
-- This invention was made with government support under grant N00014-94-1-0787 awarded by the Office of Naval Research. The government has certain rights in the invention. --

Signed and Sealed this

Fifteenth Day of January, 2002

Attest:

JAMES E. ROGAN
*Attesting Officer*  *Director of the United States Patent and Trademark Office*